United States Patent [19]

Buchwald et al.

[11] Patent Number: 4,951,672

[45] Date of Patent: Aug. 28, 1990

[54] CONTROLLED IMPEDANCE MONITORING LEAD WIRES

[75] Inventors: Randall H. Buchwald; Robert S. Stormont, both of Waukesha; Jeffrey P. Noonan, Dousman, all of Wis.

[73] Assignee: General Electric Company, Milwaukee, Wis.

[21] Appl. No.: 136,662

[22] Filed: Dec. 22, 1987

Related U.S. Application Data

[63] Continuation-in-part of Ser. No. 751,161, Jul. 2, 1985, abandoned.

[51] Int. Cl.$^5$ ............................................... A61B 5/05
[52] U.S. Cl. ............................ 128/653 SC; 128/696; 128/901
[58] Field of Search ............................ 128/639–644, 128/901, 908, 653, 696, 731

[56] References Cited

U.S. PATENT DOCUMENTS

| | | | |
|---|---|---|---|
| 4,280,507 | 7/1981 | Rosenberg | 128/696 |
| 4,494,552 | 1/1985 | Heath | 128/696 |
| 4,679,002 | 7/1987 | Sherwin et al. | 128/731 |

*Primary Examiner*—Ruth S. Smith
*Attorney, Agent, or Firm*—Douglas E. Stoner; James O. Skarsten

[57] ABSTRACT

An electrode assembly, particularly useful in nuclear magnetic resonance apparatus, for sensing a physical characteristic of a live study subject includes an electrode positioned in electrical contact with the subject for sensing the physical characteristic. The electrode assembly further includes a lead wire connected at one of its ends to the electrode and having an impedance selected to protect the study subject from heating. The impedance is also selected to have a low voltage coefficient of resistivity in order to prevent conversion of radio-frequency energy to ECG in-band energy.

9 Claims, 1 Drawing Sheet

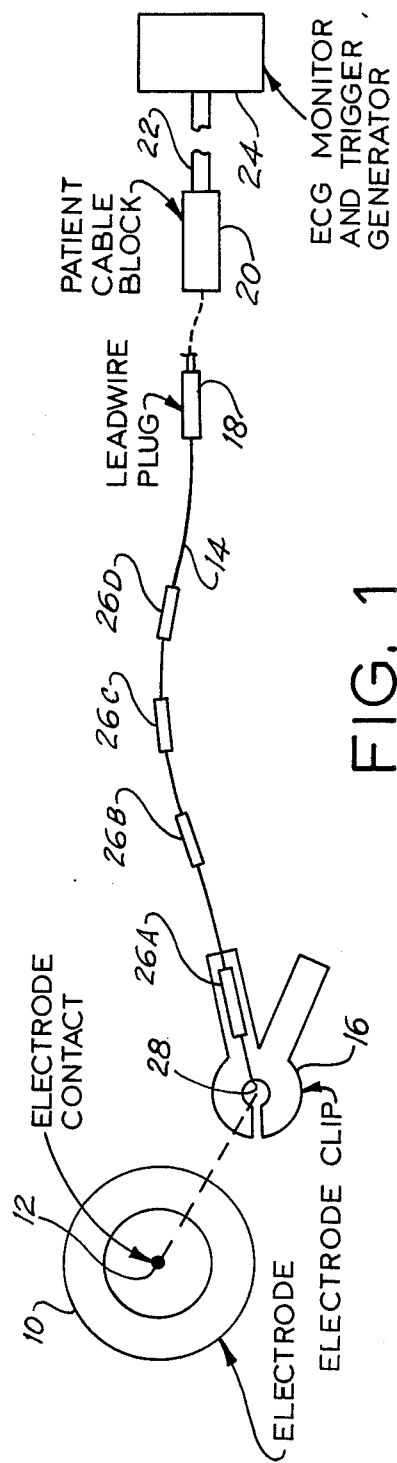
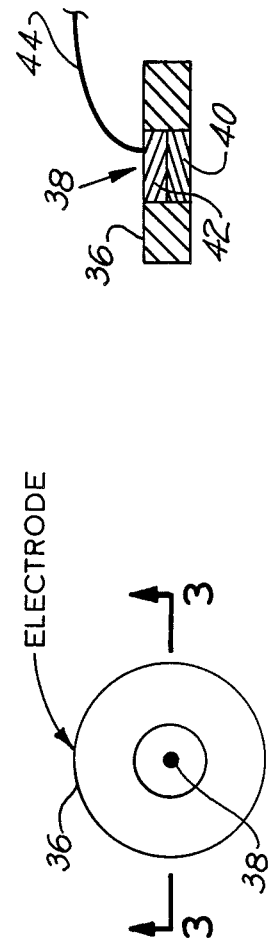

CONTROLLED IMPEDANCE MONITORING LEAD WIRES

The present application is a continuation-in-part of U.S. Ser. No. 751,161, filed July 2, 1985, now abandoned.

BACKGROUND OF THE INVENTION

This invention relates to nuclear magnetic resonance (NMR) apparatus. More specifically, this invention relates to monitoring lead wires having controlled impedance for use, for example, with NMR apparatus to monitor a physiological function, such as heart rate, of a live human or animal subject undergoing examination.

The nuclear magnetic resonance phenomenon has been utilized in the past in high resolution magnetic resonance spectroscopy instruments by structural chemists to analyze the structure of chemical compositions. More recently, NMR has been developed as a medical diagnostic modality having applications in imaging the anatomy, as well as performing in vivo, noninvasive spectroscopic analyses. As is now well known, the NMR phenomenon can be excited within a study subject positioned in a homogeneous polarizing magnetic field, having a strength of, for example, 1.5 T, by irradiating the object with radio-frequency (RF) energy at the Larmor frequency. In medical diagnostic applications, this is typically accomplished by positioning the patient to be examined in the field of an RF coil having cylindrical geometry, and energizing the RF coil with an RF power amplifier. Upon cessation of the RF excitation, the same or different RF coil is used to detect NMR signals emanating from the subject volume lying within the field of the RF coil. In the course of a complete NMR scan, a plurality of NMR signals are typically observed. The signals are used to derive NMR imaging or spectroscopic information about the subject studied.

Additionally, in typical medical imaging studies, pulsed linear magnetic field gradients are used to localize the signals to desired areas within the subject and to encode spatial information into the signals. In the course of an NMR examination, it is frequently desirable to apply pulsed magnetic field gradients in each of the X, Y, and Z directions of a conventional Cartesian coordinate system.

In some situations, it is desirable to monitor the subject during an NMR scan. This may be necessary for medical reasons in the case where the subject is an infirm patient. Another reason for monitoring the subject is to acquire signals in response to a change in a physiological characteristic of the subject and to use the signals to control some aspect of the scanning process. For example, electrocardiogram (ECG) signals can be used in a known manner as trigger signals in NMR cardiac gated studies. U.S. Pat. No. 4,413,233 entitled "Dynamic NMR Measurement," issued Nov. 1, 1983, discloses the use of trigger signals in gated NMR studies.

Typically, the gating NMR signals are acquired in a well-known manner using electrodes attached to the body of the subject. The electrodes are connected by means of electrode leads and additional cable and preamplifier as necessary to, for example, an ECG monitor. The lead wires and the cable can be modelled as a random transmission line with distributed inductance, capacitance, and resistance. The net impedance of such a transmission line varies as a function of lead wire and cable routing, placement and separation. Monitoring of the patient and acquisition of trigger signals of necessity takes place during an NMR scan so that the RF pulses and magnetic field gradient pulses can induce a current flowing in the circuit consisting of that part of the subject's body between the electrodes and the cable equivalent impedance. Thus, if the impedance at the electrode/subject body interface is higher than that of the conductors, resistive losses will occur at the interface, possibly resulting in undesirable heating of the body area in contact with the electrodes. Additionally, RF and magnetic field gradient pulses may introduce undesirable features (e.g., spikes) into the ECG signal waveform which can result in false triggering in gated studies.

It is, therefore, a principal object of the invention to provide apparatus to protect the subject of an NMR study from heating near the sight of monitoring lead contacts.

It is another object to eliminate the occurrence of false triggering resulting when radio-frequency energy is converted to low frequency energy in the monitoring lead wire.

SUMMARY OF THE INVENTION

In accordance with the invention there is provided an electrode assembly for sensing in a live study subject a physical characteristic thereof. The electrode assembly includes an electrode positionable in electrical contact with the study subject and a lead wire means connected at one of its ends to the electrode and having an impedance associated therewith to protect the study subject from heating. The impedance is selected to have a low voltage coefficient of resistivity which provides the linear transfer characteristic necessary to prevent the high frequency radio-frequency pulse from being converted to ECG in-band frequencies (the frequency band of approximately D.C. to 100 Hz). This ECG in-band energy can cause false triggers.

BRIEF DESCRIPTION OF THE DRAWINGS

The features of the invention believed to be novel are set forth with particularity in the appended claims. The invention itself, however, both as to its organization and method of operation, together with further objects and advantages thereof, may best be understood by reference to the following description taken in conjunction with the accompanying drawings in which:

FIG. 1 depicts one embodiment of the invention in which at least one discrete resistive element is placed in series with the electrode lead wire.

FIG. 2 depicts an embodiment of the invention which utilizes an electrode having an integral high impedance.

FIG. 3 is a cross section taken along line 3 of FIG. 2.

DETAILED DESCRIPTION OF THE INVENTION

In general, in accordance with the invention, it is necessary to increase the impedance of the lead wires and cables, if any, so that the resistive (IR) losses are reduced at the body/electrode interface. This can also be stated as a need to control impedance of the equivalent circuit across the electrode contacts.

Referring now to FIG. 1 there is shown a conventional electrode 10, such as a silver/silver chloride electrode, having an electrode contact 12 disposed in the central region of the electrode. A lead wire 14 is attached at one end to a lead wire clip 16 which makes contact with electrode contact 12 (as suggested by the dash lines) and at the other end to a lead wire plug 18 which electrically connects to a patient cable block 20. Patient cable block 20 is attached to one end of a cable 22 which is attached at its other end to an ECG monitor/trigger generator designated 24, which may include a preamplifier at its input.

An integral current-limiting resistor 26A is connected electrically in series with lead wire 14 and lead wire clip contact 28. Conveniently, the resistor may be fabricated integrally in the lead wire clip as shown for resistor 26A. Resistors may alternatively be connected in line with lead wire 14 anywhere along the length thereof, such as one or more resistors 26B-26D. The total resistance of resistor or resistors 26 is selected to be relatively high, such as, for example, between 33K-100K ohms. This compares with a value of 20K-100K ohms impedance at the electrode/body interface. The maximum value of the resistor is determined by the input impedance (typically 10M ohms) of the input preamplifier of the ECG monitor/trigger generator 24. Another factor which must be considered in selecting a resistor value is the possibility of creating a resistor/capacitor (RC) filter if there are capacitors, in the preamplifier input since such a filter could attenuate the ECG signal. If capacitors are not present, the resistance can be as high as 600K ohms. Consideration must also be given to the undesirable attenuative effect that too high a resistor impedance value may have on the ECG signal. In one embodiment, it has been found that a resistance value of 100K ohms performed satisfactorily. The resistor provides an additional point, other than the electrode/body interface, at which resistive power losses can be dissipated, thereby reducing any heating effects sensed by the patient.

The impedance characteristics of lead wire 14 can occasion a further problem in the presence of pulsed RF and gradient fields used in NMR studies. Specifically, the lead wire acts as a frequency converting device, due to a non-linear transfer characteristic, thereby creating ECG in-band energy when excited by radio-frequency energy. For example, during an RF spin excitation pulse, the RF waveform voltage on the lead wires is as high as 300 volts. A significant ECG in-band signal results during the RF pulse due to the altered resistance of the series resistor at this high voltage. This in turn might result in a false trigger signal or the false detection of an ECG pulse.

In accordance with the preferred embodiment of the invention, resistors 26A-26D are each comprised of resistors having a low voltage coefficient of resistivity. Simulations revealed that the coefficient should be less than about 5 parts per million per volt and is preferably about 1 ppm per volt. As a result, there is negligible ECG in-band energy appearing on the lead wires during use in conjunction with NMR studies. A preferred embodiment of each resistor 26 is a metal film resistor. Metal film resistors are commercially available and are typically comprised of a vacuum-deposited, extremely thin layer of metal alloy on a substrate. Alternatively, the resistance could be distributed over the length of the lead wire (preventing electric field nulls which cause holes in an NMR image) provided the materials voltage coefficient of resistivity was acceptable.

An alternative embodiment of the invention will be described next with reference to FIG. 2 which depicts a top view of an electrode 36 having a centrally located contact region 38. As may be best seen by reference to FIG. 3, which depicts a sectional view taken along line 3—3 in FIG. 2, contact region 38 is comprised of a high electrical conductivity electrode contact 40 and a portion 42 having a high resistance. Contact portion 42 at one of its ends is in electrical contact with high conductivity electrode contact 40 and at its other end is connected electrically to lead wire 44. The values of resistance and voltage coefficient of resistivity selected for electrode region 42 are generally the same as those discussed above for resistor 26 in FIG. 1.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

The invention claimed is:

1. An improved lead wire assembly for coupling an electrode on a subject in an NMR study to a device for monitoring an electrical signal picked up from said subject by said electrode across an electrode/subject interface having a specified impedance, said subject and said assembly proximate to a radio frequency magnetic field generated in the course of the NMR study, said assembly comprising:
   conductor means for establishing an electrically conductive path for the electrical signal between the electrode and the monitoring device;
   resistor means included in the conductive path for providing the conductive path with an impedance exceeding the specified impedance of the electrode/subject interface; and
   said resistor means having a voltage coefficient of resistivity selected to provide the conductor means with a linear transfer characteristic.

2. The assembly of claim 1 wherein the resistance of the resistor means exceeds on the order of 33k ohms.

3. The assembly of claim 1 wherein said voltage coefficient does not exceed on the order of five parts per million per volt.

4. The assembly of claim 1 wherein said voltage coefficient does not exceed on the order of 1 part per million per volt.

5. The assembly of claim 1 wherein the resistor means comprises at least one discrete resistor.

6. The assembly of claim 1 wherein the resistor means comprises at least one metal film resistor.

7. The assembly of claim 1 wherein the conductor means includes an electrode clip adapted for contacting the electrode and the resistor means comprises a discrete resistor contained within the electrode clip.

8. The assembly of claim 1 wherein the resistor means comprises a discrete resistor located at the end of the conductive path proximate to the electrode.

9. An improved lead wire assembly for coupling an electrode on a subject in an NMR study to a device for monitoring an electrical signal picked up from said subject by said electrode across an electrode/subject interface having a specified impedance, said subject and said assembly proximate to a radio frequency magnetic field generated in the course of the NMR study, said assembly comprising:
   conductor means for establishing an electrically conductive path for the electrical signal between the electrode and the monitoring device;
   resistor means included in the conductive path for providing the conductive path with an impedance exceeding the specified impedance of the electrode/subject interface; and said resistor means having a voltage coefficient of resistivity which is of a selected low value sufficient to prevent the conductor means from converting a portion of the energy of the radio frequency magnetic field into an interfering signal having a frequency lying in the frequency range of the electrical signal.

* * * * *